United States Patent [19]
Harbin et al.

[11] Patent Number: 6,004,281
[45] Date of Patent: Dec. 21, 1999

[54] METHOD AND APPARATUS FOR REGISTERING OCCUPATIONAL FITNESS

[75] Inventors: Gary Lynn Harbin, Salina; Warren Redden, Gypsum, both of Kans.

[73] Assignee: Occupational Performance Center Inc., Salina, Kans.

[21] Appl. No.: 08/951,244

[22] Filed: Oct. 16, 1997

[51] Int. Cl.$^6$ .................................................. A61B 5/00
[52] U.S. Cl. ............................................................. 600/595
[58] Field of Search ................................... 600/587, 594, 600/595; 73/379.01; 482/44, 45, 49, 91

[56] References Cited

U.S. PATENT DOCUMENTS

| | | | |
|---|---|---|---|
| 4,912,638 | 3/1990 | Pratt | 600/595 |
| 5,271,416 | 12/1993 | Lepley | 600/595 |
| 5,348,519 | 9/1994 | Prince et al. | 482/6 |
| 5,373,858 | 12/1994 | Rose et al. | 600/595 |
| 5,697,869 | 12/1997 | Ehrenfried et al. | 482/6 |

*Primary Examiner*—Max Hindenburg
*Attorney, Agent, or Firm*—Hovey, Williams, Timmons & Collins

[57] ABSTRACT

A method an apparatus for testing the strength of an individual to determine occupational fitness is provided which receives physical strength inputs from a tested individual for storage in a computer memory and comparison to predetermined standards. The apparatus includes a frame carrying two or more strength monitoring stations, each including a load cell, the stations being mounted at different positions on the frame. Each of the stations is electronically connected to a computer. The computer sequentially receives signals from load cells within the computer's memory corresponding to preselected strength tests. The method includes having the tested individual apply a force to a first member coupled to a load cell and storing in the computer memory a value corresponding to the force applied, then having the individual apply a second force to a second member coupled to a second load cell and transmitting a second value corresponding to the second force to the computer memory, and then comparing the first value and the second value to predetermined occupational performance values to determine the tested individual's occupational fitness. In preferred embodiments, the method includes performing a plurality of different tests and then combining the values and then storing and comparing the values to determine the individual's occupational fitness.

26 Claims, 4 Drawing Sheets

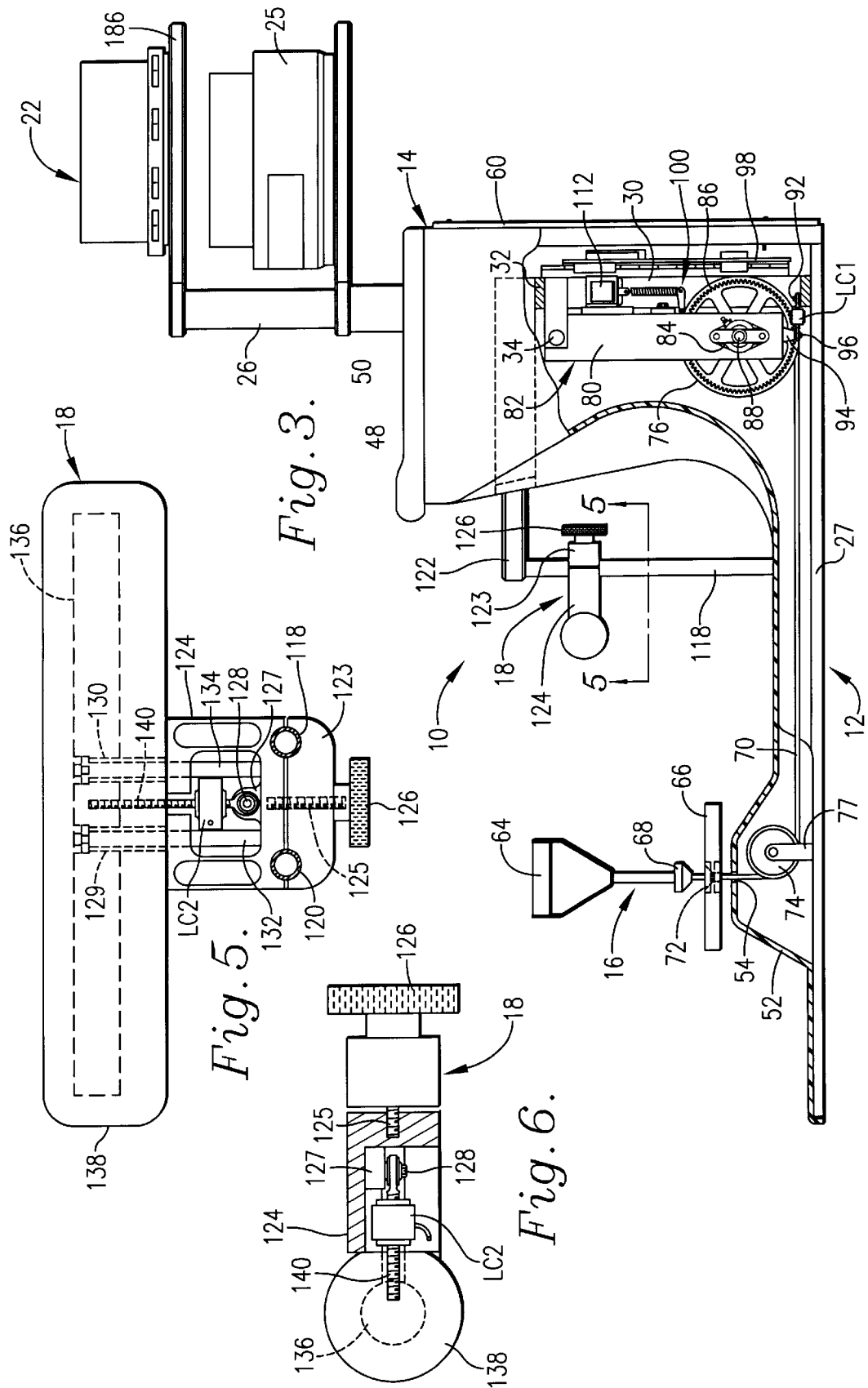

METHOD AND APPARATUS FOR REGISTERING OCCUPATIONAL FITNESS

BACKGROUND OF THE INVENTION

1. Field of the Invention

This invention broadly concerns a method and apparatus for measuring the strength of individuals through various testing regimens and providing a baseline to determine how the individual can best be placed according to physical capabilities. More particularly, it is concerned with an apparatus which is capable of measuring a plurality of discrete isometric strength performance characteristics of individuals of differing stature and directly inputting those measurements into an electronic storage device.

2. Description of the Prior Art

When hiring individuals to work in any environment which may have physical requirements associated with the job to be performed, it is beneficial to try and match the individual with a position within his or her physical capabilities. The U.S. Department of Labor has established a Dictionary of Occupational Titles, which includes 5 levels for which a strength factor is expressed. These include sedentary work, light work, medium work, heavy work and very heavy work, with increasing levels of physical demands. Each level includes a description of the amount of force or strength which must be performed in the job, and the frequency of application. Additional factors include the amount of time an individual may be required to stand or walk. For example, under the category "Occupations in assembly, installation, and repair of large household appliances and similar commercial and industrial equipment", the description indicates that only light work would be anticipated for the description number 827.131-010 "Electrical-Appliance-Service Supervisor", while heavy work would be anticipated for the description number 827.361-014 "Refrigeration Mechanic".

There has developed a need for objectively determining an individual's strength and capacity to meet such standards or for any other job necessitating physical tasks. This type of determination preferably involves collecting more than a single strength measurement, such as several strength measurements for discrete body regions in an objective, repeatable manner without risking injury to the tested individual. Moreover, there has developed a need for a device which readily accommodates individuals of various body sizes to perform the same tests. Furthermore, there has developed a need for a testing instrument which can quickly receive input for a variety of different discrete muscles or muscle groups without elaborate changeover procedures. There has developed a need for an apparatus which can efficiently store and process physical testing for occupational suitability. Finally, there has developed a need for a method and apparatus which can collect the testing input and quickly and effectively transmit the testing results to a remote site for analysis.

SUMMARY OF THE INVENTION

These and other objects have largely been met by the method and apparatus according to the present invention. The method and apparatus hereof provides an effective means for measuring the physical abilities of individuals in order to best match the individual to the available job, or to avoid injury to an individual hired to perform relatively heavy work. As a collateral benefit, the testing information may assist employers in establishing a baseline of physical capability for their employees to identify overly stressful positions in terms of physical demands or to evaluate workman's compensation claims.

The apparatus of the present invention includes a plurality of strength monitoring stations which are adjustably mounted on a frame. Each station is provided with a load cell which, when a force is applied by a testee, transmits information to a data storage device. The strength monitoring stations may perform a single test or be adaptable for testing a plurality of different strength characteristics. The data storage device is connected to a modem, printer or other output device for providing the testing information in a report format for use and analysis. In preferred embodiments, the data storage device includes a computer, which sequences the activation of the strength monitoring stations. In particularly preferred embodiments, the computer is electronically connected to at least one of the strength monitoring stations to actuate an adjustment mechanism when the individual is properly positioned for performing the desired test. The adjustment mechanism for one of the stations includes a pulley connected to a linkage provided with a solenoid for locking the pulley in position to permit the load applied by the testee to be carried by the load cell when the testee is in the proper position and for automatically repeating the position.

The method of the present invention broadly includes administering a plurality of different strength tests to a testee, sequentially measuring a strength load characteristic for each such test on a load sensing monitor, and transmitting data corresponding to the measured characteristic for each such test to a data storage device. Preferably, the tests are performed in a predetermined sequence in order to provide consistent results, most preferably using an apparatus which electronically stores the information as the test is performed. The strength load characteristics are preferably directly inputed to the data storage device contemporaneously with performance of each test by electronic means. The method further preferably includes adjusting the positioning of the strength monitoring station to the individual testee at the testing location. In particularly preferred embodiments, the stored measured characteristics are further transmitted to a receiver remote from the testing site.

BRIEF DESCRIPTION OF THE DRAWINGS

FIG. 3 is a left side elevational view in partial vertical cross section along line 3—3 of FIG. 2 with the arm strength station removed and showing the linkage and pulley arrangement for the lifting station;

FIG. 5 is a enlarged fragmentary horizontal cross-sectional view taken along line 5—5 of FIG. 3 to show the mounting for the leg extension station;

FIG. 6 is an enlarged fragmentary elevational view of the leg extension station in partial vertical cross-section to illustrate the mounting of the load cell therewith;

DESCRIPTION OF THE PREFERRED EMBODIMENT

Figure 1:
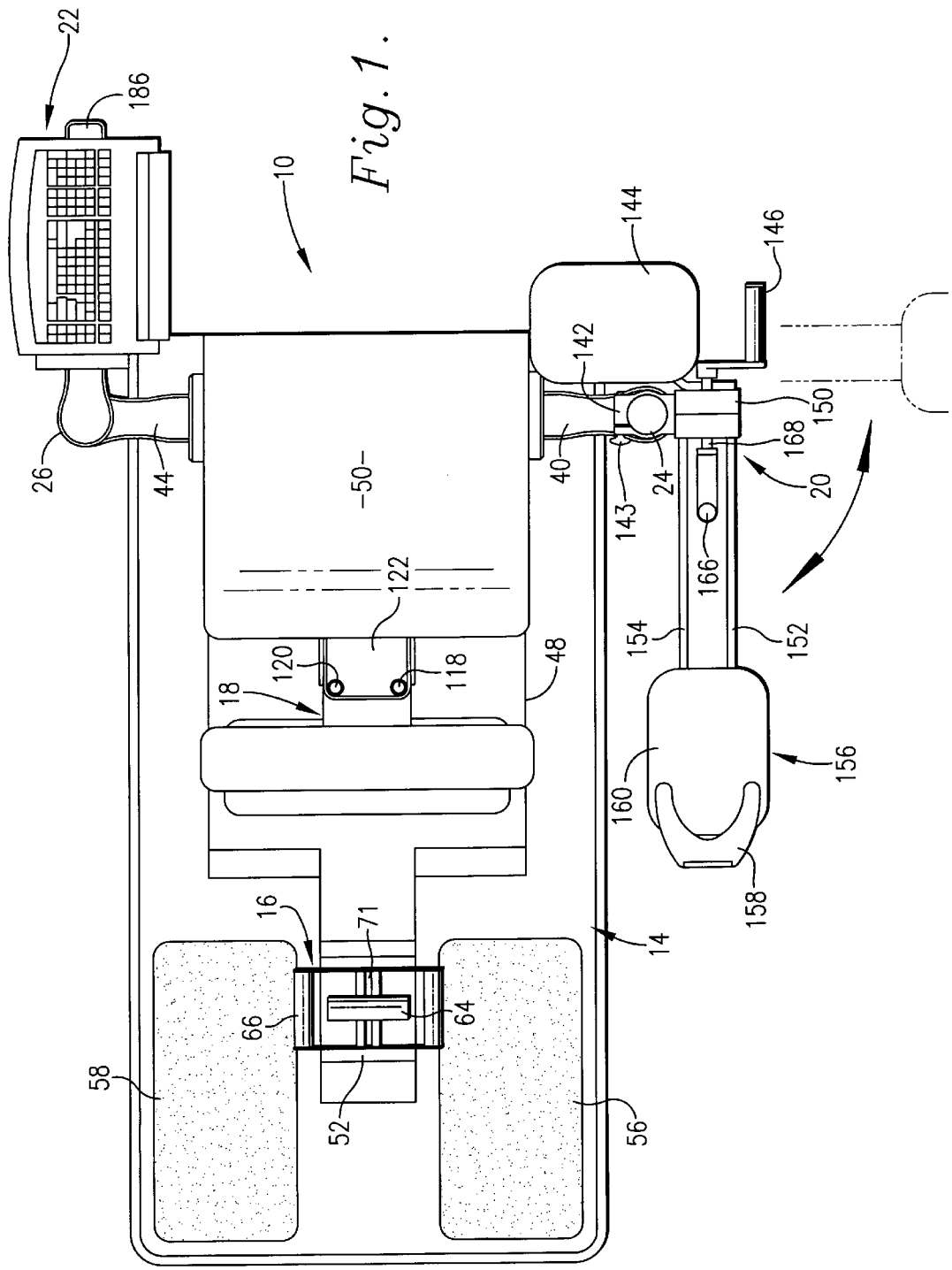
FIG. 1 is a top plan view of the testing apparatus in accordance with the present invention, showing a leg extension station, a lifting station, and an arm strength station, with the latter illustrated in an alternate position in phantom.

Referring now to the drawing, a strength testing apparatus 10 for determining occupational fitness as shown herein broadly includes a frame 12, a cover 14 mounted on the frame 10, a first strength monitoring station 16, a second strength monitoring station 18, a third strength monitoring station 20, and a computer 22 for controlling the apparatus 10 storing external and internally generated data received from the strength monitoring stations 16, 18 and 20, and outputting the data in printed or electronic format. The frame 12 includes a first column 24 mounting the third strength monitoring station 20 and a second column 26 mounting the computer 22 and a printer 25 which is electronically coupled to the computer 22 by a conventional cable.

In greater detail, the frame 12 includes a base 27 which rests on a floor or other supporting structure, upright supports 28 and 30 connected to the base 27, crossbeam 32 connected to the tops of supports 28 and 30, and pivot bar 34 suspended beneath the crossbeam 32 by hangers 36 and 38. The frame 12 also includes cantilever beams 40 and 42 connecting first column 24 to upright support 28 and cantilever beams 44 and 46 connecting second column 26 to upright support 30.

The frame receives thereon cover 14 which is of molded synthetic resin material which may be glass fiber reinforced. The cover 14 includes platform 48 which is elevated relative to the base 27 and preferably provided with a cushion 50 for permitting a tested individual to sit thereon. A raised portion 52 is also positioned rearwardly of the platform 48 and provided with an opening 54 therethrough, with non-skid surfaces 56 and 58 positioned on each side of the raised portion 52 as shown in FIG. 1. A panel 60 is removably mounted by set screws or the like to the cover 14 for permitting access to the front side 62 of the apparatus 10.

First strength monitoring station 16 includes a single hand handle 64 and double-hand handle 66. The single-hand handle 64 is provided with an inverse cone-shaped stop 68 coupling the handle 64 to a cable 70. The double-hand handle 66 is provided with an slot 71 through which the cable 70 may pass, and a recess 72 complementally configured with stop 68, whereby upward movement of the double-hand handle 66 engages the stop 68 to place the cable 70 in tension. The cable 70 is routed through opening 54 of raised portion 52 which accommodates a pulley 74 rotatably mounted to forks 77 which are in turn secured to the base 27. The cable 70 is entrained around pulley 74 and thereby directed to reel 76.

Reel 76 is rotatably mounted on shaft 78 passing through arm 80 of carriage 82. Arm 80 is swingably mounted on pivot bar 34. The arm 80 mounts a bearing block 84 for permitting free rotation of the reel 76 on carriage 82. A sprocket 86 is fixedly coupled to the reel 76 and rotatably carried therewith. A cable reel potentiometer 88 is coupled to the arm 80 and receives shaft 78 therethrough for counting the number or rotations of the reel 76. A spring loaded rewind 90 is also fixedly coupled to the reel 76 by bolts or the like and presents an upwardly oriented extension engaging a rod 91 secured to the arm 80 for maintaining the internal spring within the rewind in tension for rewinding the cable 70 when tension thereon is released and the reel is unlocked.

Figure 4:
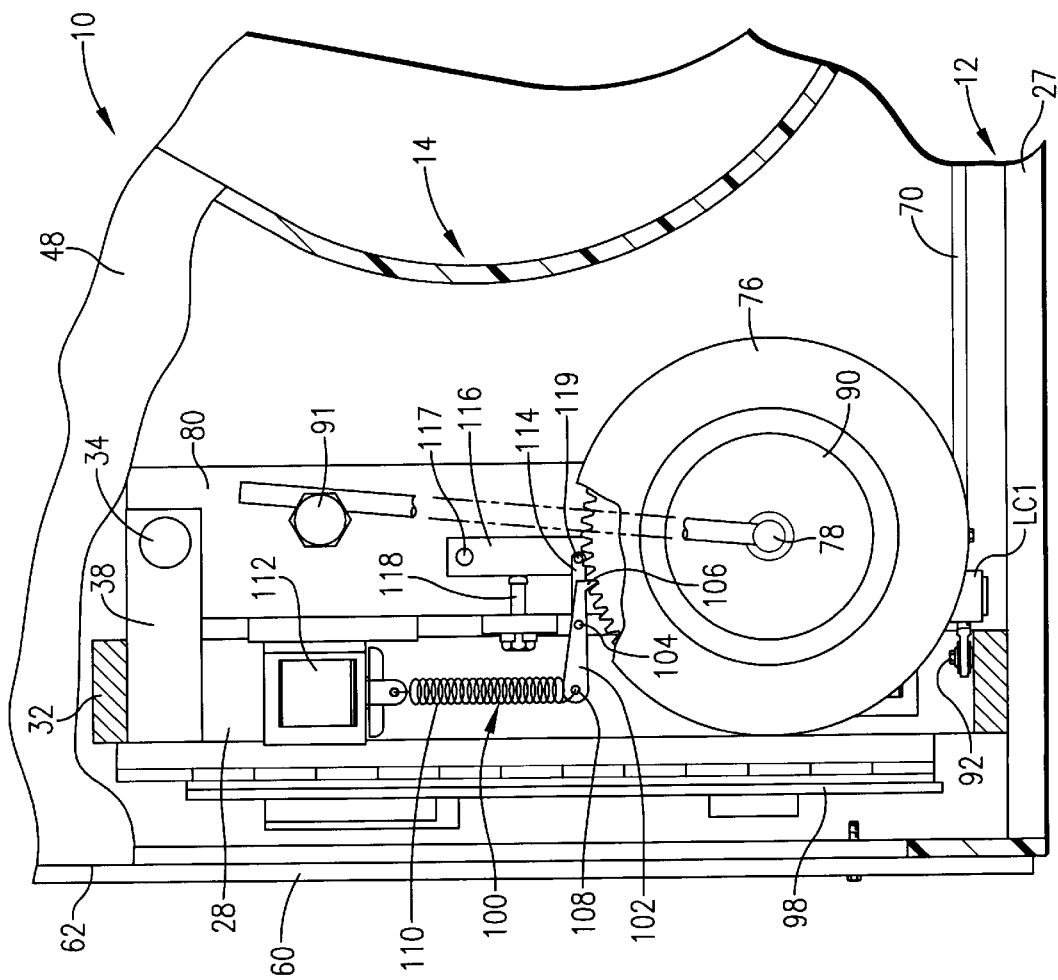
FIG. 4 is an enlarged fragmentary vertical cross-sectional view taken along line 4—4 of FIG. 2 with portions of the rewind pulley removed to show the locking pawl engaged with a sprocket for transmitting lifting loads to the corresponding load cell.

First strength monitoring station 16 further includes a first load cell LC1 anchored by bolt 92 to base 27. Load cell LC1 is also coupled to a foot 94 depending from and connected to arm 80 of carriage 82 by a threaded coupler such as bolt 96. The load cells herein are preferably rated at 300 pounds, and each is electrically coupled to computer 24 through circuit board 98. First strength monitoring station also includes a lock 100 which inhibits the reel 76 from rotation when engaged. The lock 100 includes a locking toggle 102 pivotally mounted on pivot pin 104 on arm 80. The toggle 102 presents a pawl 106 at the rear end for engagement with the teeth of sprocket 86 as shown in FIG. 4. The front end of the toggle 102 is provided with hole 108 which receives spring 110. The spring 110 connects the toggle 102 to solenoid 112 mounted on arm 80 such that the weight of the front end of the toggle lifts the pawl 106 out of engagement with the sprocket 86 when the solenoid 112 is unenergized. When the solenoid 112 is energized and retracts upwardly, it places spring 110 in tension to pivot the pawl 106 into locking engagement with the sprocket 86.

Link 114 swingably connects pivot pin 104 to block 116 on arm 80. Block 116 is fixed at its upper end by a pin 117 to arm 80 and is connected to link 114 by another pin 119 to link 114. The block 116 is positioned for engaging a damper 118 mounted on upright support 30. The damper 118 presents a resilient tip for resisting impact due to the limited swinging movement of the arm 80 during tensioning and release of the cable 70.

Second strength monitoring station 18 is adjustably mounted on bars 118 and 120 connected to frame 12 at their bottom ends and by header 122 secured by bolts extending through the cover 14 to a bar connected to beams extending rearwardly from crossbeam 34 connected to upright supports 28 and 30. The station 18 includes a receiver 123 and a block 124 interconnected by bolt 125 which passes through receiver 123. The receiver may be tightened by the bolt 125 to bring the receiver 123 and the block 124 into engagement with bars 118 and 120 as shown in FIG. 5 by turning threaded knob 126. The block 124 includes a nose 127 which receives therethrough a bolt 128 mounting second load cell LC2 thereon. The block also presents two parallel guide rods 132 and 134. The guide rods 132 and 134 are secured at their front end to block 124 but are freely shiftably received within respective channels 129 and 130 of engagement member 136 which is covered with padding 138. The load cell LC2 is provided with rearwardly extending threaded rod 140 which is threadably coupled to engagement member 136, whereby force applied to the engagement member in a direction parallel to guide rods 132 and 134 is carried by second load cell LC2 which is fixed to nose 127.

Figure 2:
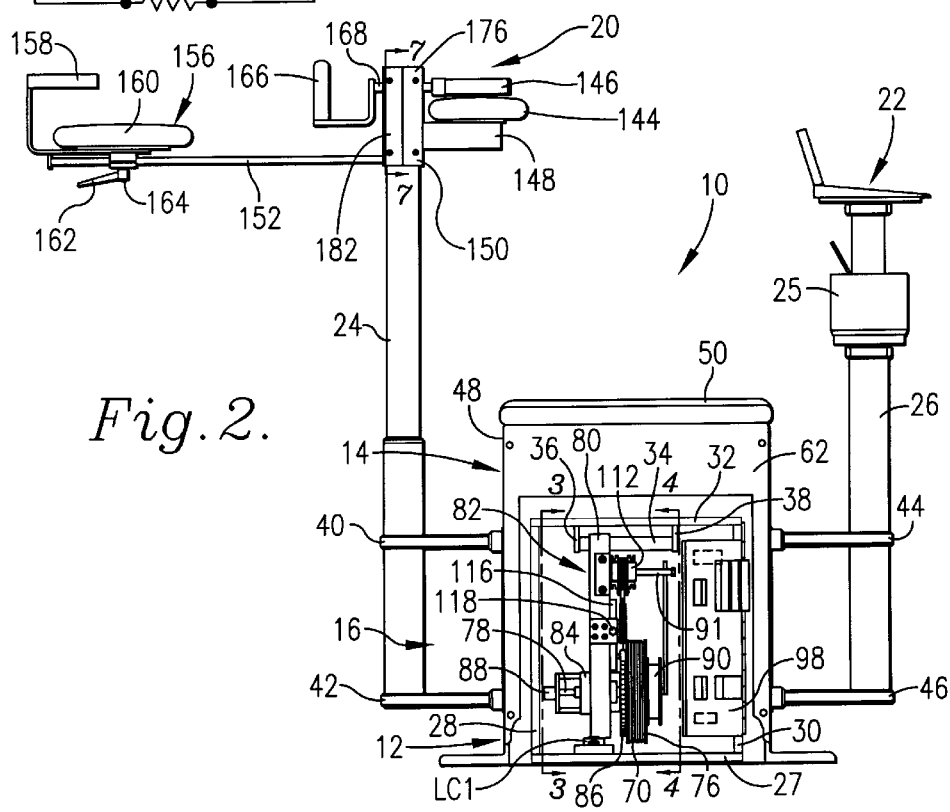
FIG. 2 is a front elevational view thereof, showing the arm strength station pivoted to the position shown in phantom in FIG. 2 and a covering panel removed to show the pulley and linkage of the lifting station.

Third strength monitoring station 20 is swingably carried on column 24 for movement about a vertical axis as illustrated in FIGS. 1 and 2. The third station 20 includes a clamp 142 held to column 24 by a set screw 143, thereby permitting vertical translational adjustment along column 24 as well as swinging movement about a vertical axis, and permits the third station 20 to be secured in position once properly placed to accommodate a particular patient. Third station 20 further includes a wrist pad 144 positioned adjacent lever 146. The wrist pad 144 is supported by mount 148 connected to housing 150. Rails 152 and 154 are cantilevered from the opposite side of housing 150 and adjustably carry elbow support 156 for movement therealong. The elbow support 156 includes upper arm brace 158 and elbow pad 160. The elbow support 156 may be clamped at a desired position along rails 150 and 152 by lever clamp 162 carried on a threaded rod 164. A grip 166 is oriented from housing 150 toward elbow support 156. A shaft 168 mounts both grip 166 and lever 146 thereon.

Figure 7:
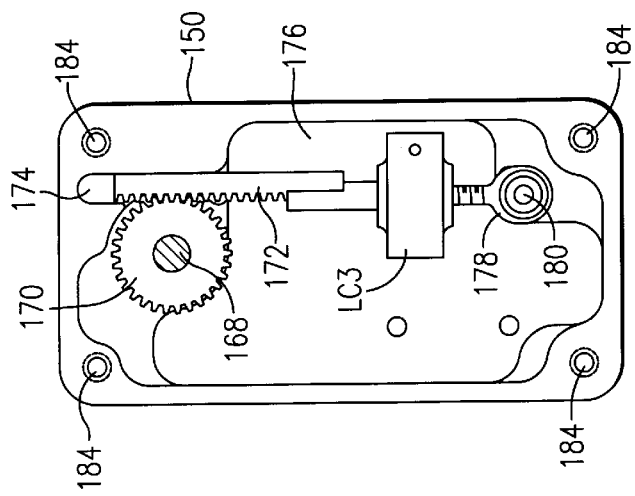
FIG. 7 is an enlarged fragmentary vertical cross-sectional view taken along the line 7—7 of FIG. 2 showing the rack and pinion connection between the arm strength crank and its corresponding load cell.

As may be seen in FIG. 7, the shaft 168 also mounts pinion gear 170 thereon. Pinion gear 170 is engaged with rack 172 shiftably received within slot 174 of first side 176 of housing 150. Rack 172 is connected to third load cell LC3, which is secured to housing 150 by threaded eye 178 by bolt 180. A second side 182 of housing 150 is mounted to first side 176 by four alien screws received within threaded openings 184 to enclose pinion gear 170, rack 172 and third load cell LC3 within housing 150.

The computer 22 is carried on a support 186 of second column 26 and may be of any conventional type preferably having both soft and hard disk drives and random access memory and central processing unit, such as an NEC notebook computer having an Intel 486 or Pentium processor and capable of running and provided with DOS or Windows software for an operating system. The computer 22 is preferably provided with a modem 188 and is also coupled at its serial port to a printer 25 for outputting the results of testing.

Figure 8:
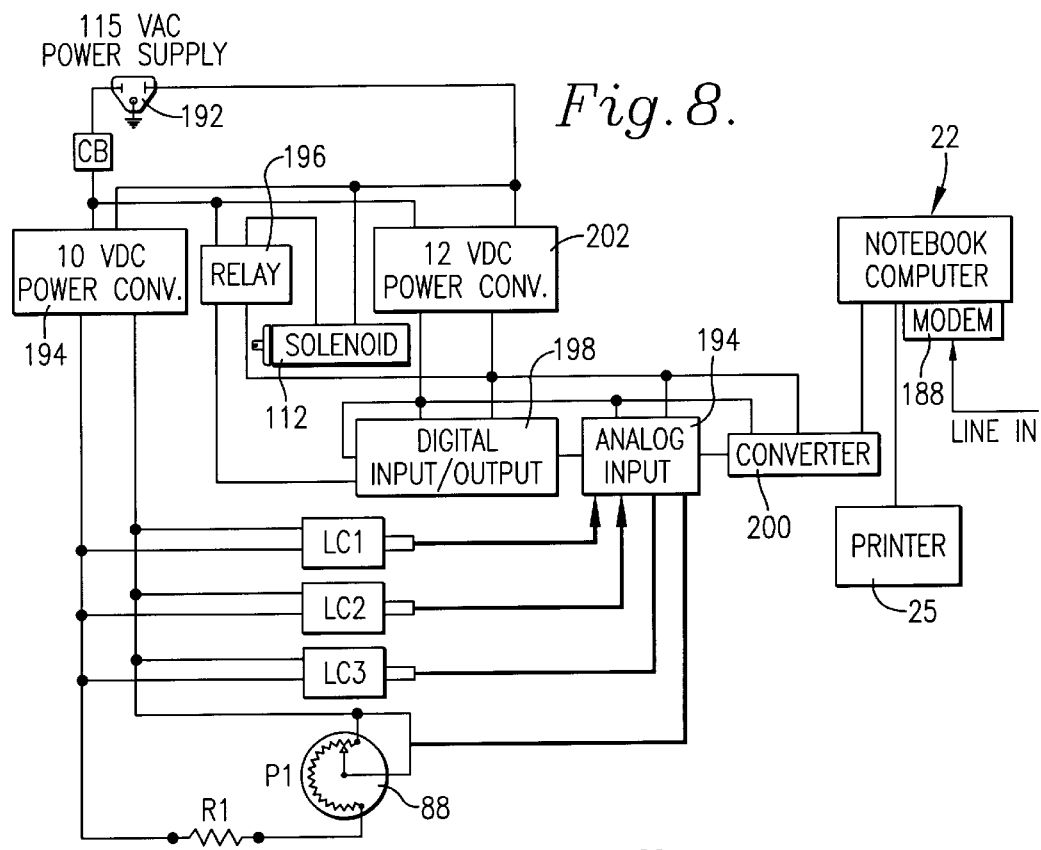
FIG. 8 is an electrical schematic diagram illustrating the components of the control, data storage, output and measurement system of the present invention.

The computer 22 serves both to control the sequence and operation of the apparatus 10 as well as to receive and store data received from the load cells LC1, LC2 and LC3. FIG. 8 is an electrical schematic diagram showing the electrical circuitry for the apparatus. A 115 volt AC power supply 192 supplies the necessary power input for operation of the apparatus 10, and a circuit breaker CB prevents circuit overloading. The 110 volt AC current is converted to 10 volt DC current for excitation voltage supplied to the load cells LC1, LC2 and LC3 and to the cable reel potentiometer 88 by power converter 194. The current supplied to the potentiometer 88 first passes through a conventional 470K ohm resistor R1. The signals from the load cells LC1, LC2 and LC3 and by potentiometer 88 are passed to an analog input 194 by a conventional twisted wire pairs.

The 12 volt DC AC current is also supplied to a solid state relay 196 which is activated by keystroke input to the computer 24 to energize the solenoid 112 which locks the reel when energized. The relay 196 is connected to the analog input 194 as well as to a digital input/output device 198 and an RS-232 to RS-485 serial/parallel converter 200. The converter 200 is connected to one serial port of the computer 22, and another serial port is connected to the printer 25. The analog input 194 is also connected to each the digital input/output device 198 and converter 200 by parallel cable connections. A 12 volt DC power converter 202 also receives power from the 115 AC power supply 192 and is connected to the relay 196 and the analog input 194, the digital input/output device 198 and the converter 200 to supply 12 volt DC current. A telephone line is connected to the modem 188 for communication with a remote computer.

In use, the apparatus 10 is designed to receive identifying information and physical parameter inputs from the operator regarding the tested individual prior to the performance of physical input by the tested individual to the strength monitoring stations 16, 18 and 20. The input may be typed or otherwise input by, e.g., diskette or modem, into the computer 22 and may include height, weight, heart rate, systolic and diastolic blood pressure, body fat and spirometry measurements. In addition, the tested individual may perform other tests such as range of motion, grip or pinch tests on a hand dynamometer or lifting capacity on external weights, and exercises such as situps and squats which the operator may input into the database for the individual being tested and evaluated. Other health history factors may be typed or otherwise inputted into the database such as whether the individual has had prior surgery, heart attacks, angina, epilepsy or seizures, asthma, bronchitis, or is a smoker, The operator then activates the load cells for each of the stations in sequence to receive their input as the individual performs the physical tests. The tests may be performed in any desired sequence and different tests may be performed using the apparatus 10. The following tests and sequences are illustrative rather than exhaustive of the possible sequencing and tests which may be performed. Prior to beginning testing and periodically thereafter, each load cell LC1, LC2 and LC3 is calibrated using a known standard, such as a weight, so that the signal generated thereby is indicative of the force generated by the tested individual.

The tested individual may start at the third strength testing station by placing the right arm in the elbow support 156 with the upper arm received in the brace 158 and the forearm resting on the elbow pad 160. The elbow support 156 is adjustable toward or away from the grip 166 for the tested individuals physical features by moving the elbow support along the rails 152 and 154 and then locked into position by lever clamp 162. The vertical position of the elbow support 156 may be adjusted vertically to accommodate individuals of different heights by releasing the set screw holding the clamp 142, sliding the clamp along the column 24, and then refighting the clamp 142. The right hand grasps the grip 166 and the individual then exerts a wrist supination force, attempting to turn the grip 166 in a clockwise direction. All of the exercises are isometric rather than dynamic, and the third load cell LC3 registers both the maximum force, preferably that exerted without pain, and the maximum force averaged over the number of trials, each testing interval preferably lasting at least three seconds. The wrist supination test is received, and the computer queries the operator whether the data is to be saved. If the operator enters a keystroke "Y" (or other entry corresponding to the affirmative answer "yes") to save, the computer then sequences the apparatus to store the data in memory and perform the next test. The next test may be wrist pronation for the right wrist with the right arm in the same position, and the tested individual then performs an isometric application of force to the grip 166 attempting to turn the grip in a counterclockwise direction for the right wrist. As with the wrist supination test, the wrist pronation test is preferably performed twice and the operator, if satisfied, keys the computer to save the data which reflects both the maximum and the average of the maximum forces exerted over the number of trials, each preferably lasting at least three seconds. The tested individual then places his or her left arm in the elbow support 156 and the wrist supination and wrist pronation tests are repeated for the left arm.

The next tests which may be performed on the third station of the apparatus are wrist flexion tests for the right and left wrists, in sequence. The right forearm is placed on the wrist pad 144 and the tested individual grasps the lever 146 with the right hand and attempts to flex and bring the wrist upward while maintaining the forearm on the wrist pad 144. As with the other tests performed on the apparatus 10, the test requires isometric rather than dynamic force, and is repeated. If the tests were satisfactorily performed, the operator enters a "Y" or other keystroke corresponding to an affirmative answer on the computer to save the data including the maximum force and maximum force values averaged over the number of the trials, each of which are preferably at least three seconds in duration, and sequence to the next test. If the test was unsatisfactorily performed, the operator keys a "N" or other negative entry and the data in the computer memory corresponding to the test is deleted and the test is repeated. Once a successful test has its data saved, the computer advances to the next sequence; here the same wrist flexion test is then performed for the left wrist as described hereinabove.

The application of force to either the grip 166 or the lever 146 transfers force to the shaft 168. The shaft is fixed to the pinion gear 170 so that the force is then transmitted to the rack 172. The rack 172 transmits the force to the load cell LC3, which is fixed and yields only slightly to the applied force, so that the testing is isometric or static rather than dynamic. The load cell LC3 then generates a signal, transmitted to the computer 22, corresponding to the force applied.

The next test in the sequence may be performed at the first strength monitoring station 16 and may be a elbow flexion test. The tested individual stands on the non-skid surfaces 56 and 58 and grasps the single hand handle 64, then flexes the right arm to position the forearm at a 90 degree angle to the upper arm. In pulling on the handle 64, the cable 70 is withdrawn from reel 76 and the cable reel potentiometer 88 counts the number of rotations of the reel. Once properly position, the operator enters a keystroke to save the position of the handle 64 on the computer and energize the solenoid 112. The solenoid 112 retracts and exerts a force on spring 110 which lifts front end of toggle 102 and drops the pawl 106 to lock with sprocket 86. So locked, the sprocket 86, which is fixed to the reel 76, prevents the reel 76 from turning and thus fixes the extent to which handle 64 may be lifted. The pawl 106 also locks the reel 76 against rotation relative to arm 80. Thus, any force exerted on handle 64 tensioning the cable 70 is transmitted to the arm 80. The arm 80, being swingably mounted on the pivot bar 34, is connected at foot 94 to load cell LC1. Thus, the force applied to the handle 64 by the tested individual is transmitted to the load cell LC1, which in turn transmits a signal to computer 24 corresponding to the force applied. After the tested individual lifts on handle 64 with the right arm for the required duration, preferably at least three seconds, the handle 64 is released and the rewind 90 retracts some or all of the cable onto the reel. When the test is repeated, the computer 24 has saved the number of rotations of reel 76 measured by the potentiometer 88 and re-engages the pawl 106 automatically to lock the reel at the same position, thereby putting the handle 64 at the same location. After the second application of force and query from the computer, the operator enters a keystroke "Y" or other affirmative keystroke to save the data as to the maximum force and maximum force averaged over the number of the trials. The test is then repeated for the left bicep as set forth above. When each application of force is released, the pawl 106 disengages and the arm swings forwardly with the impact absorbed by the resilient end of damper 118. The position of the handle 64 is automatically saved by the computer 24 between the first and second performance of each test, so that the computer 24 automatically signals the solenoid 112 to re-engage the pawl 106 when the potentiometer detects that the cable 70 has been withdrawn an equivalent distance to the first application of force in the test. Thus, the first and second application of force for the test of each arm is performed with the handle 64 in the same position.

The next test may be performed at the second strength monitoring station 18, which is adapted for quadracep strength measurements for seated leg extension. The tested individual sits on the cushion 50 with legs bent so that the shin is positioned behind the padding over engagement member 136. The tested individual is instructed to try to extend his or her legs, thereby applying force to the engagement member 136. The engagement member 136, free to move along guide rods 132 and 134, transmits the applied force to load cell LC2. The load cell LC2 is fixed at its front end to nose 127 and held by block 124 to bars 118 and 120, so that the load applied is substantially static, and the test is isometric. As in the aforementioned tests, the force is applied in preferably two or more discrete applications, and the operator keystrokes "Y" or other affirmative entry to save the maximum force and maximum force averaged over the number of the trials.

Subsequent testing may be sequentially performed at the first strength monitoring station for, for example, shoulder (deltoid muscle) strength. The tested individual raises single hand handle 64 with the right arm to position the handle level with the shoulder and the arm fully extended. The operator then enters a keystroke on the computer 24 to signal the solenoid 112 to engage the pawl 106 to thereby lock the reel 76 against further movement. As with the bicep test, the isometric lifting force applied to the handle 64 is transmitted through the cable 70 to the arm 80, and then to load cell LC1, which sends a corresponding signal to the computer 24. The force is released and the pawl 106 disengages, permitting the cable reel rewind 90 to return all or a portion of the cable 70 to the reel 76. The test is then repeated, with the memory of the computer 24 receiving an input signal from the potentiometer 88 to activate the solenoid to engage the pawl 106 and lock the reel 76 in the same position as in the first application of force for that test. The tested individual then repeats the test, attempting to lift the handle 64 with the individual's arm extended, applying the force for the required duration which is preferably at least three seconds. When the test has been completed, the computer again queries the operator whether the data is to be saved, and upon entry of an affirmative keystroke response, the computer saves the maximum force and maximum force averaged over the number of the trials. The computer then saves the data and sequences the data base to activate the desired test next in sequence. In this case, the shoulder strength (deltoid muscle) test is then repeated for the left arm.

The final two tests are then performed at the first strength monitoring station 16. These include a torso lift, with the legs straight and the back bent so that the arms are extended, with the tested individual standing on the non-skid surfaces 56 and 58 and the arms extended so that each hand is holding onto the double-hand handle 66. When the double-hand handle 66 is raised, it engages the stop 68 and pulls a portion of the cable 70 from the reel 76. The operator then enters a keystroke so that the number of turns of the reel 76 recorded by the potentiometer will be saved by the computer 24 and the solenoid 112 will automatically activate to lock the reel as described above. After the second torso lift is performed, the computer 24 will query the operator whether to save the data, and an affirmative entry will save the data and sequence the next test. In the described method, the next and final test would be a bent knee squat performed with the knees bent, the arms extended to grasp the double-hand handle 66 and the back substantially erect. The operation of the apparatus 10 and the entry of the data is the same as previously described.

Once all data is entered for a tested individual, a report may be generated by the computer. This reporting may be accomplished by use of the printer or by transmission to a remote location by telephone line and modem, or both. Typically, the information is transmitted by modem prior to a printed report being generated. The report is available for review by, for example, a physician such as an orthopedic surgeon or an appropriate occupational health specialist. When all the data has been considered, the reviewer may recommend that the individual be retained in the desired position, moved to a different position according to the individual's physical capability or perform job hardening for the desired position, or terminated because the individual is not capable of performing the job and may not be accommodated in another job for which a vacancy exists.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention. For example, the number of trials and the duration of testing intervals may be varied.

The inventors hereby state their intent to rely on the Doctrine of Equivalents to determine and assess the reasonably fair scope of their invention as pertains to any apparatus not materially departing from but outside the literal scope of the invention as set out in the following claims.

We claim:

1. An apparatus for testing strength of independent muscle groups of a tested person, said apparatus comprising:
   a frame;
   first and second strength monitoring stations mounted to said frame and remotely located thereon relative to one another, each of said first and second strength monitoring stations including respective first and second load cells for generating respective first and second force application signals;
   a first engagement member coupled to said first load cell and configured for engagement by one body part of the tested person in applying a force by a first muscle group;
   a second engagement member coupled to said second load cell and configured for engagement by another body part of the tested person in applying a force by a second muscle group;
   at least one of said first and second load cells being connected to said engagement member to prevent substantial translational movement of the respective first or second engagement member relative to said frame; and
   a computer operatively connected to said first and second load cells for sequentially receiving said first and second force-application signals and for storing data corresponding to said signals.

2. The apparatus as set forth in claim 1, said computer being remote from said frame.

3. The apparatus as set forth in claim 2, said computer operably connected to a modem for receiving and sending data corresponding to said generated signals.

4. The apparatus as set forth in claim 1, each of said load cells being coupled to said frame to inhibit translational movement of said load cell and said engagement members during testing.

5. The apparatus as set forth in claim 1, said first engagement member including a handle.

6. The apparatus as set forth in claim 5, said first strength monitoring station further including an adjustable cable operatively connected to said first engagement member and said first load cell, said cable configured for adjustably positioning said engagement member relative to said first load cell.

7. The apparatus as set forth in claim 6, wherein said cable is operatively connected to an arm swingably mounted to said frame and coupled to said first load cell.

8. The apparatus as set forth in claim 7, including a reel rotatably mounted to said arm for carrying said cable thereon.

9. The apparatus as set forth in claim 8, further including a sprocket fixedly coupled to said reel and rotatably carried therewith.

10. The apparatus as set forth in claim 7, including a locking mechanism carried by said arm for selectively inhibiting said cable from rotation.

11. The apparatus as set forth in claim 10, said locking mechanism including a solenoid operatively coupled to said computer.

12. The apparatus as set forth in claim 11, further including a potentiometer coupled between said arm and said wheel for measuring the rotatable positioning of the reel relative to the arm, said potentiometer being operatively coupled to said computer for providing a signal to said computer corresponding to said measured relative rotatable position.

13. The apparatus as set forth in claim 12, said first strength monitoring station further including a rewind mechanism for biasing said reel in a cable-retrieving direction.

14. The apparatus as set forth in claim 11, said locking mechanism further including a lock toggle operable coupled with said arm, said locking toggle including a pawl lockably engageable with said sprocket.

15. An apparatus as set forth in claim 1, said second strength monitoring station further comprising a block adjustable mounted to said frame and shiftably receiving thereon said second engagement member.

16. An apparatus as set forth in claim 15, said second load cell mechanically connectable with said block and said second load cell.

17. An apparatus as set forth in claim 15, said second strength monitoring station further comprising a rack fixed to said second load cell and a pinion gear in engagement with said rack and operably connected to said second engagement member, whereby application of said force to said second engagement member is transmitted thorough said pinion gear and said rack to said second load cell.

18. An apparatus as set forth in claim 17, said second strength monitoring station further comprising an adjustable limb support operatively coupled to said frame.

19. An apparatus as set forth in claim 18, said second strength monitoring station further comprising a fourth engagement member operatively coupled with said second load cell.

20. An apparatus as set forth in claim 19, said second and fourth engagement members including grips configured for isometric wrist pronation, isometric wrist flexion and isometric elbow flexion.

21. An apparatus as set forth in claim 1 further comprising:
   a third load cell fixedly coupled to said frame; and
   a third engagement member operable for receiving a third force by the tested person operably connected to said third load cell, said third load cell generating a third signal corresponding to said force applied by the tested person to said third engagement member and said third load cell being operatively coupled to said computer.

22. An apparatus as set forth in claim 21, said third strength monitoring station further comprising a seat mounted on said frame and spaced from said third engagement member.

23. A strength testing apparatus for measuring the physical strength of a tested individual comprising at least one strength monitoring station, said strength monitoring station including a force receiving member, a load cell, a frame mounting said load cell, a linkage connecting the force receiving member to the load cell, said linkage including a cable coupled to said force receiving member, a reel for storing a portion of said cable thereon, a carriage rotatably carrying said reel, a pivot coupled to said frame for swingably mounting said carriage, a selectively actuateable lock mounted on said carriage for holding said reel against rotation and including a pawl, a sprocket mounted for rotation with said reel and a solenoid adapted for selectively shifting said pawl into and out of engagement with said sprocket, and a coupler operatively connecting said carriage to said load cell.

24. The apparatus as set forth in claim 23, said strength testing apparatus further comprising a support configured for supporting a body part while applying a force.

25. A method for measuring occupation fitness of a tested individual comprising the steps of:

having the tested individual apply a first force to a first force engaging member operatively coupled to a first load cell, said first force corresponding to a first motion;

generating a first signal at said first load cell corresponding to said first force;

transmitting said first signal to a computer having a memory storing a first value corresponding to said first signal in the memory of said computer;

having the tested individual apply a second force to a second force engaging member remote from said first force engaging member operatively coupled to a second load cell, said second force corresponding to a second motion;

generating a second signal at said second load cell corresponding to said second force;

transmitting said second signal to said computer;

storing a second value corresponding to said second signal in the memory of the computer; and comparing said first value and said second value to pre-determined occupation performance values to comparatively determine the tested individual's occupation fitness corresponding to each said motion.

26. The method of claim 25 further including the step of applying said first and second forces in a predetermined sequence.

* * * * *